US008481080B2

(12) United States Patent
Longin et al.

(10) Patent No.: US 8,481,080 B2
(45) Date of Patent: Jul. 9, 2013

(54) METHOD OF CROSS-LINKING HYALURONIC ACID WITH DIVINULSULFONE

(75) Inventors: Fanny Longin, Frederiksberg (DK); Khadija Schwach-Abdellaoui, Frederiksberg (DK)

(73) Assignee: Novozymes Biopolymer A/S, Bagsvaerd (DK)

( * ) Notice: Subject to any disclaimer, the term of this patent is extended or adjusted under 35 U.S.C. 154(b) by 899 days.

(21) Appl. No.: 11/719,790

(22) PCT Filed: Nov. 24, 2005

(86) PCT No.: PCT/DK2005/000753
§ 371 (c)(1), (2), (4) Date: May 21, 2007

(87) PCT Pub. No.: WO2006/056204
PCT Pub. Date: Jun. 1, 2006

(65) Prior Publication Data
US 2009/0155362 A1 Jun. 18, 2009

Related U.S. Application Data

(60) Provisional application No. 60/630,620, filed on Nov. 24, 2004.

(30) Foreign Application Priority Data

Nov. 24, 2004 (DK) .................................. 2004 01824

(51) Int. Cl.
*A61K 9/10* (2006.01)
(52) U.S. Cl.
USPC ........................................................ 424/484

(58) Field of Classification Search
None
See application file for complete search history.

(56) References Cited

U.S. PATENT DOCUMENTS

| 4,141,973 | A | * | 2/1979 | Balazs | 514/54 |
|---|---|---|---|---|---|
| 4,582,865 | A | | 4/1986 | Balazs et al. | |
| 4,713,448 | A | | 12/1987 | Balazs et al. | |
| 4,957,744 | A | | 9/1990 | Della Valle et al. | |
| 5,017,229 | A | | 5/1991 | Burns et al. | |
| 6,013,679 | A | | 1/2000 | Kuo et al. | |
| 6,831,172 | B1 | | 12/2004 | Barbucci et al. | |
| 2003/0175902 | A1 | * | 9/2003 | Sloma et al. | 435/84 |

FOREIGN PATENT DOCUMENTS

| EP | 0 244 987 | 6/1987 |
|---|---|---|
| EP | 161 887 | 9/1991 |

(Continued)

OTHER PUBLICATIONS

Material Safety Data Sheet for Vinyl Sulfone, Nov. 2008.*
Qi-Sheng et al, Hyaluronic Acid and Clinical Medicine, Second Military Medical University Press, Section V: Drug Sustained Release Systems and Table 8-9, 3 pages. (2003).
Tezel et al, Journal of Cosmetic and Laser Therapy, vol. 10, pp. 35-42 (2008).

*Primary Examiner* — Brian Gulledge
(74) *Attorney, Agent, or Firm* — Jason Garbell; Eric J. Fechter

(57) ABSTRACT

The present invention relates to methods of producing a homogenous hydrogel comprising hyaluronic acid, or salt thereof, crosslinked with divinylsulfone (DVS), said method comprising the steps of (a) providing an alkaline solution of hyaluronic acid, or salt thereof; (b) adding DVS to the solution of step (a), whereby the hyaluronic acid, or salt thereof, is crosslinked with the DVS to form a gel; (c) treating the gel of step (b) with a buffer, wherein the gel swells and forms a hydrogel comprising hyaluronic acid, or salt thereof, crosslinked with DVS.

21 Claims, 5 Drawing Sheets

FOREIGN PATENT DOCUMENTS

| | | | |
|---|---|---|---|
| WO | WO 86/00079 | * | 1/1986 |
| WO | WO 00/27887 | | 5/2000 |
| WO | WO 03/089476 | | 10/2003 |
| WO | WO 2004/067575 | | 8/2004 |
| WO | WO 2005/066215 | | 7/2005 |
| WO | WO 2005/112888 | | 12/2005 |

* cited by examiner

METHOD OF CROSS-LINKING HYALURONIC ACID WITH DIVINULSULFONE

CROSS-REFERENCE TO RELATED APPLICATIONS

This application is a 35 U.S.C. 371 national application of PCT/DK2005/000753 filed Nov. 24, 2005, which claims priority or the benefit under 35 USC. 119 of Danish application no. PA 2004 01824 filed Nov. 24, 2004 and U.S. provisional application No. 60/630,620 filed Nov. 24, 2004, the contents of which are fully incorporated herein by reference.

BACKGROUND

The present invention relates to a process for the preparation of modified hyaluronic acid (HA), in particular cross-linked HA, for use in cosmetic, biomedical and pharmaceutical applications.

Hyaluronic acid (HA) is a natural and linear carbohydrate polymer belonging to the class of the non-sulfated glycosaminoglycans. It is composed of beta-1,3-N-acetyl glucosamine and beta-1,4-glucuronic acid repeating disaccharide units with a molecular weight (MW) up to 6 MDa. HA is present in hyaline cartilage, synovial joint fluid, and skin tissue, both dermis and epidermis. HA may be extracted from natural tissues including the connective tissue of vertebrates, from the human umbilical cord and from cocks combs. However, it is preferred today to prepare it by microbiological methods to minimize the potential risk of transferring infectious agents, and to increase product uniformity, quality and availability (US 2003/0175902, Novozymes).

Numerous roles of HA in the body have been identified. It plays an important role in the biological organism, as a mechanical support for the cells of many tissues, such as the skin, tendons, muscles and cartilage. HA is involved in key biological processes, such as the moistening of tissues, and lubrication. It is also suspected of having a role in numerous physiological functions, such as adhesion, development, cell motility, cancer, angiogenesis, and wound healing. Due to the unique physical and biological properties of HA (including viscoelasticity, biocompatibility, biodegradability), HA is employed in a wide range of current and developing applications within cosmetics, ophthalmology, rheumatology, drug delivery, wound healing and tissue engineering. The use of HA in some of these applications is limited by the fact that HA is soluble in water at room temperature, i.e. about 20° C., it is rapidly degraded by hyaluronidase in the body, and it is difficult to process into biomaterials. Cross-linking of HA has therefore been introduced in order to improve the physical and mechanical properties of HA and its in vivo residence time.

U.S. Pat. No. 4,582,865 (Biomatrix Inc.) describes the preparation of cross-linked gels of HA, alone or mixed with other hydrophilic polymers, using divinyl sulfone (DVS) as the cross-linking agent. The preparation of a cross-linked HA or salt thereof using a polyfunctional epoxy compound is disclosed in EP 0 161 887 B1. Other bi- or poly-functional reagents that have been employed to cross-link HA through covalent linkages include formaldehyde (U.S. Pat. No. 4,713,448, Biomatrix Inc.), polyaziridine (WO 03/089476 A1, Genzyme Corp.), L-aminoacids or L-aminoesters (WO 2004/067575, Biosphere S.P.A.). Carbodiimides have also been reported for the cross-linking of HA (U.S. Pat. No. 5,017,229, Genzyme Corp.; U.S. Pat. No. 6,013,679, Anika Research, Inc). Total or partial cross-linked esters of HA with an aliphatic alcohol, and salts of such partial esters with inorganic or organic bases, are disclosed in U.S. Pat. No. 4,957,744.

SUMMARY OF THE INVENTION

A problem to be solved by the present invention is how to manufacture hyaluronic acid based hydrogels with improved properties, such as higher homogeneity, increased softness, and/or easier syringeability.

The cross-linked gels produced by the method of the invention show an increased homogeneity and an increased softness compared to the standard DVS crosslinked HA-hydrogels. The gels resulting from the method of the instant invention are also easier to inject through a syringe, as shown in the examples.

Accordingly, in a first aspect the invention relates to a method of producing a hydrogel comprising hyaluronic acid, or salt thereof, crosslinked with divinylsulfone (DVS), said method comprising the steps of:
(a) providing an alkaline solution of hyaluronic acid, or salt thereof;
(b) adding DVS to the solution of step (a), whereby the hyaluronic acid, or salt thereof, is crosslinked with the DVS to form a gel;
(c) treating the gel of step (b) with a buffer, wherein the gel swells and forms a hydrogel comprising hyaluronic acid, or salt thereof, crosslinked with DVS.

In a second aspect, the invention relates to a hydrogel comprising hyaluronic acid, or salt thereof, crosslinked with divinylsulfone (DVS), which is sufficiently homogenous to be injected from a 1 ml syringe through a 27G½ needle over a distance of 55 mm at a speed of 12.5 mm/min with a stable injection force, which after the initial 40 seconds of the injection and until the syringe is empty, varies no more than about 5 Newton (N), preferably no more than about 4 N, more preferably 3 N, 2 N, or most preferably no more than about 1 N.

In a third aspect, the invention relates to a composition comprising a hydrogel as defined in the second aspect, and an active ingredient, preferably the active ingredient is a pharmacologically active agent.

A fourth aspect of the invention relates to a pharmaceutical composition comprising an effective amount of a hydrogel as defined in the second aspect, together with a pharmaceutically acceptable carrier, excipient or diluent.

A fifth aspect relates to a pharmaceutical composition comprising an effective amount of a hydrogel as defined in the second aspect as a vehicle, together with a pharmacologically active agent.

A sixth aspect relates to a cosmetic article comprising as an active ingredient an effective amount of a hydrogel as defined in the second aspect or a composition as defined in any of the third, fourth, or fifth aspects.

In a seventh aspect, the invention relates to a sanitary, medical or surgical article comprising a hydrogel as defined in the second aspect or a composition as defined in any of the third, fourth, or fifth aspects, preferably the article is a diaper, a sanitary towel, a surgical sponge, a wound healing sponge, or a part comprised in a band aid or other wound dressing material.

An important aspect relates to a medicament capsule or microcapsule comprising a hydrogel as defined in the second aspect or a composition as defined in any of the third, fourth, or fifth aspects.

A number of aspects relate to uses of a hydrogel as defined in the second aspect or a composition as defined in any of the third, fourth, or fifth aspects, for the manufacture of a medicament for the treatment of osteoarthritis, cancer, the manufacture of a medicament for an opthalmological treatment, the manufacture of a medicament for the treatment of a wound, the manufacture of a medicament for angiogenesis, the manufacture of a medicament for the treatment of hair loss or baldness, the manufacture of a moisturizer or a cosmetic, or in a cosmetic treatment.

DEFINITIONS

The term "hyaluronic acid" is used in literature to mean acidic polysaccharides with different molecular weights constituted by residues of D-glucuronic and N-acetyl-D-glucosamine acids, which occur naturally in cell surfaces, in the basic extracellular substances of the connective tissue of vertebrates, in the synovial fluid of the joints, in the endobulbar fluid of the eye, in human umbilical cord tissue and in cocks' combs.

The term "hyaluronic acid" is in fact usually used as meaning a whole series of polysaccharides with alternating residues of D-glucuronic and N-acetyl-D-glucosamine acids with varying molecular weights or even the degraded fractions of the same, and it would therefore seem more correct to use the plural term of "hyaluronic acids". The singular term will, however, be used all the same in this description; in addition, the abbreviation "HA" will frequently be used in place of this collective term.

"Hyaluronic acid" is defined herein as an unsulphated glycosaminoglycan composed of repeating disaccharide units of N-acetylglucosamine (GlcNAc) and glucuronic acid (GlcUA) linked together by alternating beta-1,4 and beta-1,3 glycosidic bonds. Hyaluronic acid is also known as hyaluronan, hyaluronate, or HA. The terms hyaluronan and hyaluronic acid are used interchangeably herein.

Rooster combs are a significant commercial source for hyaluronan. Microorganisms are an alternative source. U.S. Pat. No. 4,801,539 discloses a fermentation method for preparing hyaluronic acid involving a strain of Streptococcus zooepidemicus with reported yields of about 3.6 g of hyaluronic acid per liter. European Patent No. EP0694616 discloses fermentation processes using an improved strain of Streptococcus zooepidemicus with reported yields of about 3.5 g of hyaluronic acid per liter. As disclosed in WO 03/054163 (Novozymes), which is incorporated herein in its entirety, hyaluronic acid or salts thereof may be recombinantly produced, e.g., in a Gram-positive Bacillus host.

Hyaluronan synthases have been described from vertebrates, bacterial pathogens, and algal viruses (DeAngelis, P. L., 1999, Cell. Mol. Life Sci. 56: 670-682). WO 99/23227 discloses a Group I hyaluronate synthase from Streptococcus equisimilis. WO 99/51265 and WO 00/27437 describe a Group II hyaluronate synthase from *Pasturella multocida*. Ferretti et al. discloses the hyaluronan synthase operon of *Streptococcus pyogenes*, which is composed of three genes, hasA, hasB, and hasC, that encode hyaluronate synthase, UDP glucose dehydrogenase, and UDP-glucose pyrophosphorylase, respectively (Proc. Natl. Acad. Sci. USA. 98, 4658-4663, 2001). WO 99/51265 describes a nucleic acid segment having a coding region for a *Streptococcus equisimilis* hyaluronan synthase.

Since the hyaluronan of a recombinant *Bacillus* cell is expressed directly to the culture medium, a simple process may be used to isolate the hyaluronan from the culture medium. First, the *Bacillus* cells and cellular debris are physically removed from the culture medium. The culture medium may be diluted first, if desired, to reduce the viscosity of the medium. Many methods are known to those skilled in the art for removing cells from culture medium, such as centrifugation or microfiltration. If desired, the remaining supernatant may then be filtered, such as by ultrafiltration, to concentrate and remove small molecule contaminants from the hyaluronan. Following removal of the cells and cellular debris, a simple precipitation of the hyaluronan from the medium is performed by known mechanisms. Salt, alcohol, or combinations of salt and alcohol may be used to precipitate the hyaluronan from the filtrate. Once reduced to a precipitate, the hyaluronan can be easily isolated from the solution by physical means. The hyaluronan may be dried or concentrated from the filtrate solution by using evaporative techniques known to the art, such as lyophilization or spraydrying.

Host Cells

A preferred embodiment relates to the method of the first aspect, wherein the hyaluronic acid or salt thereof is recombinantly produced, preferably by a Gram-positive bacterium or host cell, more preferably by a bacterium of the genus *Bacillus*.

The host cell may be any *Bacillus* cell suitable for recombinant production of hyaluronic acid. The *Bacillus* host cell may be a wild-type *Bacillus* cell or a mutant thereof. Bacillus cells useful in the practice of the present invention include, but are not limited to, *Bacillus agaraderhens, Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells. Mutant *Bacillus subtilis* cells particularly adapted for recombinant expression are described in WO 98/22598. Non-encapsulating *Bacillus* cells are particularly useful in the present invention.

In a preferred embodiment, the *Bacillus* host cell is a *Bacillus amyloliquefaciens, Bacillus clausii, Bacillus lentus, Bacillus licheniformis, Bacillus stearothermophilus* or *Bacillus subtilis* cell. In a more preferred embodiment, the *Bacillus* cell is a *Bacillus amyloliquefaciens* cell. In another more preferred embodiment, the *Bacillus* cell is a *Bacillus clausii* cell. In another more preferred embodiment, the *Bacillus* cell is a *Bacillus lentus* cell. In another more preferred embodiment, the *Bacillus* cell is a *Bacillus licheniformis* cell. In another more preferred embodiment, the *Bacillus* cell is a *Bacillus subtilis* cell. In a most preferred embodiment, the *Bacillus* host cell is *Bacillus subtilis* A164Δ5 (see U.S. Pat. No. 5,891,701) or *Bacillus subtilis* 168Δ4.

Molecular Weight

The content of hyaluronic acid may be determined according to the modified carbazole method (Bitter and Muir, 1962, *Anal Biochem*. 4: 330-334). Moreover, the average molecular weight of the hyaluronic acid may be determined using standard methods in the art, such as those described by Ueno et al., 1988, *Chem. Pharm. Bull*. 36, 4971-4975; Wyatt, 1993, *Anal. Chim. Acta* 272: 140; and Wyatt Technologies, 1999, "Light Scattering University DAWN Course Manual" and "DAWN EOS Manual" Wyatt Technology Corporation, Santa Barbara, Calif.

In a preferred embodiment, the hyaluronic acid, or salt thereof, of the present invention has a molecular weight of about 10,000 to about 10,000,000 Da. In a more preferred embodiment it has a molecular weight of about 25,000 to about 5,000,000 Da. In a most preferred embodiment, the hyaluronic acid has a molecular weight of about 50,000 to about 3,000,000 Da.

In a preferred embodiment, the hyaluronic acid or salt thereof has a molecular weight in the range of between 300,000 and 3,000,000; preferably in the range of between 400, 000 and 2,500,000; more preferably in the range of between 500,000 and 2,000,000; and most preferably in the range of between 600,000 and 1,800,000.

In yet another preferred embodiment, the hyaluronic acid or salt thereof has a low average molecular weight in the range of between 10,000 and 800,000 Da; preferably in the range of between 20,000 and 600,000 Da; more preferably in the range of between 30,000 and 500,000 Da; even more preferably in the range of between 40,000 and 400,000 Da; and most preferably in the range of between 50,000 and 300,000 Da.

Salts and Crosslinked HA

A preferred embodiment relates to a method of the first aspect, which comprises an inorganic salt of hyaluronic acid, preferably sodium hyaluronate, potassium hyaluronate, ammonium hyaluronate, calcium hyaluronate, magnesium hyaluronate, zinc hyaluronate, or cobalt hyaluronate.

Other Ingredients

In a preferred embodiment, the product produced by the method of the invention may also comprise other ingredients, preferably one or more active ingredient, preferably one or more pharmacologically active substance, and also preferably a water-soluble excipient, such as lactose or a non-biologically derived sugar.

Non-limiting examples of an active ingredient or pharmacologically active substance which may be used in the present invention include vitamin(s), protein and/or peptide drugs, such as, human growth hormone, bovine growth hormone, porcine growth hormone, growth hormone releasing hormone/peptide, granulocyte-colony stimulating factor, granulocyte macrophage-colony stimulating factor, macrophage-colony stimulating factor, erythropoietin, bone morphogenic protein, interferon or derivative thereof, insulin or derivative thereof, atriopeptin-III, monoclonal antibody, tumor necrosis factor, macrophage activating factor, interleukin, tumor degenerating factor, insulin-like growth factor, epidermal growth factor, tissue plasminogen activator, factor IIV, factor IIIV, and urokinase.

A water-soluble excipient may be included for the purpose of stabilizing the active ingredient(s), such excipient may include a protein, e.g., albumin or gelatin; an amino acid, such as glycine, alanine, glutamic acid, arginine, lysine and a salt thereof; carbohydrate such as glucose, lactose, xylose, galactose, fructose, maltose, saccharose, dextran, mannitol, sorbitol, trehalose and chondroitin sulphate; an inorganic salt such as phosphate; a surfactant such as TWEEN® (ICI), poly ethylene glycol, and a mixture thereof. The excipient or stabilizer may be used in an amount ranging from 0.001 to 99% by weight of the product.

Several aspects of the invention relate to various compositions and pharmaceuticals comprising, among other constituents, an effective amount of the crosslinked HA product, and an active ingredient, preferably the active ingredient is a pharmacologically active agent; a pharmaceutically acceptable carrier, excipient or diluent, preferably a water-soluble excipient, and most preferably lactose.

A preferred embodiment of the invention relates to products or compositions of the invention comprised in an effervescent tablet, which may otherwise be formulated as described in the art. For instance, an effervescent tablet may comprise citric acid, sodium bicarbonate, and an oligosaccharide or other sugar. Effervescent tablets are easy to store, and with the fast-dissolving product of the present invention, they are quickly dissolved and thus provide an ideal means of oral administration.

In addition, aspects of the invention relate to articles comprising a product as defined in the first aspect or a composition as defined in the aspects and embodiments above, e.g., a cosmetic article, a sanitary article, a medical or surgical article. In a final aspect the invention relates to a medicament capsule or microcapsule comprising a product as defined in the first aspect or a composition as defined in other aspects and embodiments of the invention.

FIGURES

Figure 3:
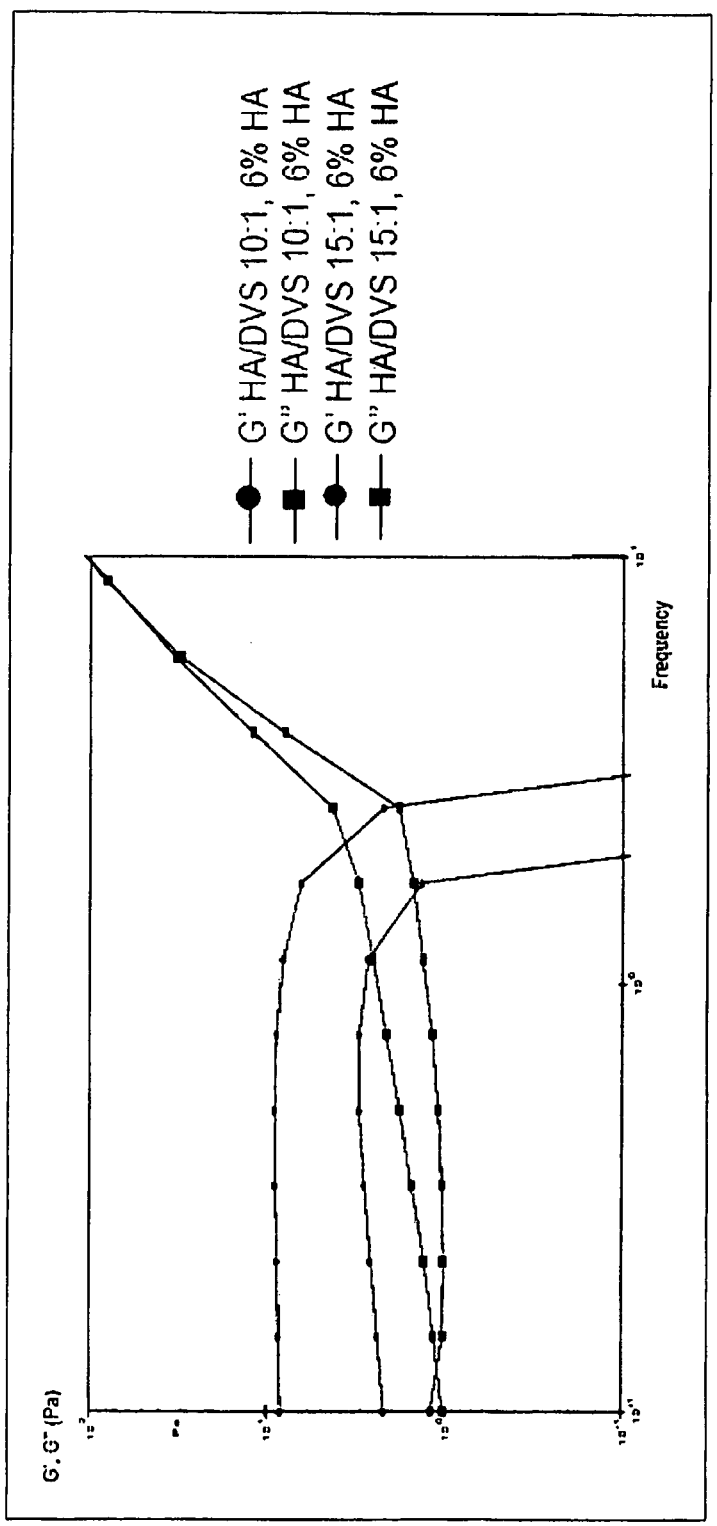

FIG. 3 shows the elastic modulus (G'), labelled with a circle, and the shear loss or viscous modulus (G''), labelled with a square, of two HA hydrogels prepared according to the invention, one prepared with a HA/DVS ratio of 10:1 and 6% HA, and the other with a HA/DVS ratio of 15:1 and 6% HA, as described in detail in example 7 below. The elastic modulus (G': circle) of the HA/DVS 10:1 hydrogel is the upper line (y-axis) at all frequencies (x-axis), and the shear loss modulus (G'': square) of the HA/DVS 10:1 hydrogel is the lower line, except at the extreme left-hand side of the x-axis, where it is the upper line.

Figure 4:
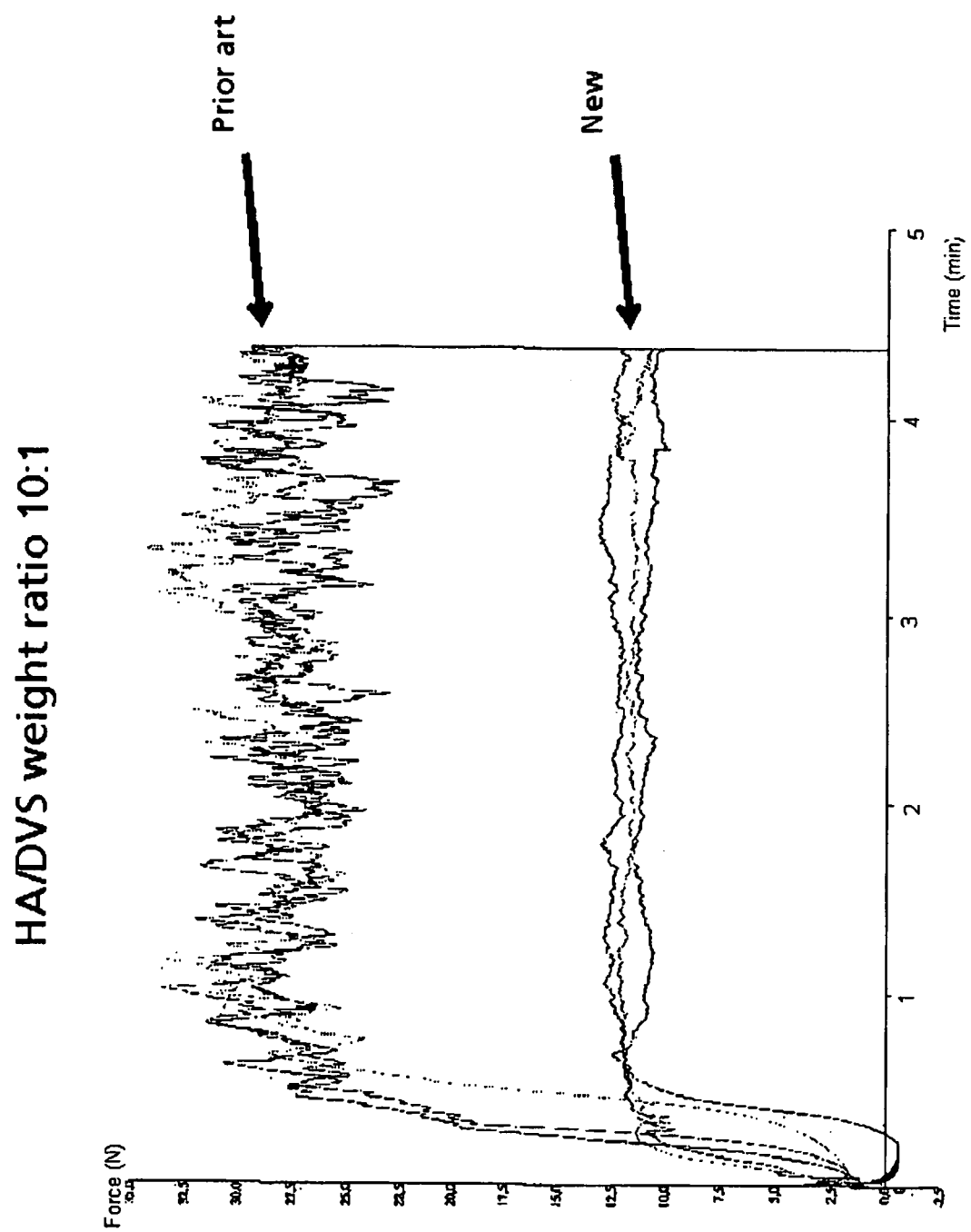

FIG. 4 shows the syringeability of DVS cross-linked HA hydrogels (HA/DVS 10:1, wt) prepared following the process described in example 2 herein ('new, heated'), and a hydrogel prepared according to the prior art (see U.S. Pat. No. 4,582,865, example 1) without heating, as described in example 9 below. The y-axis shows the injection force in Newton, beginning at 0.0 with increments of 2.5, and ending at 35.0.

Figure 5:
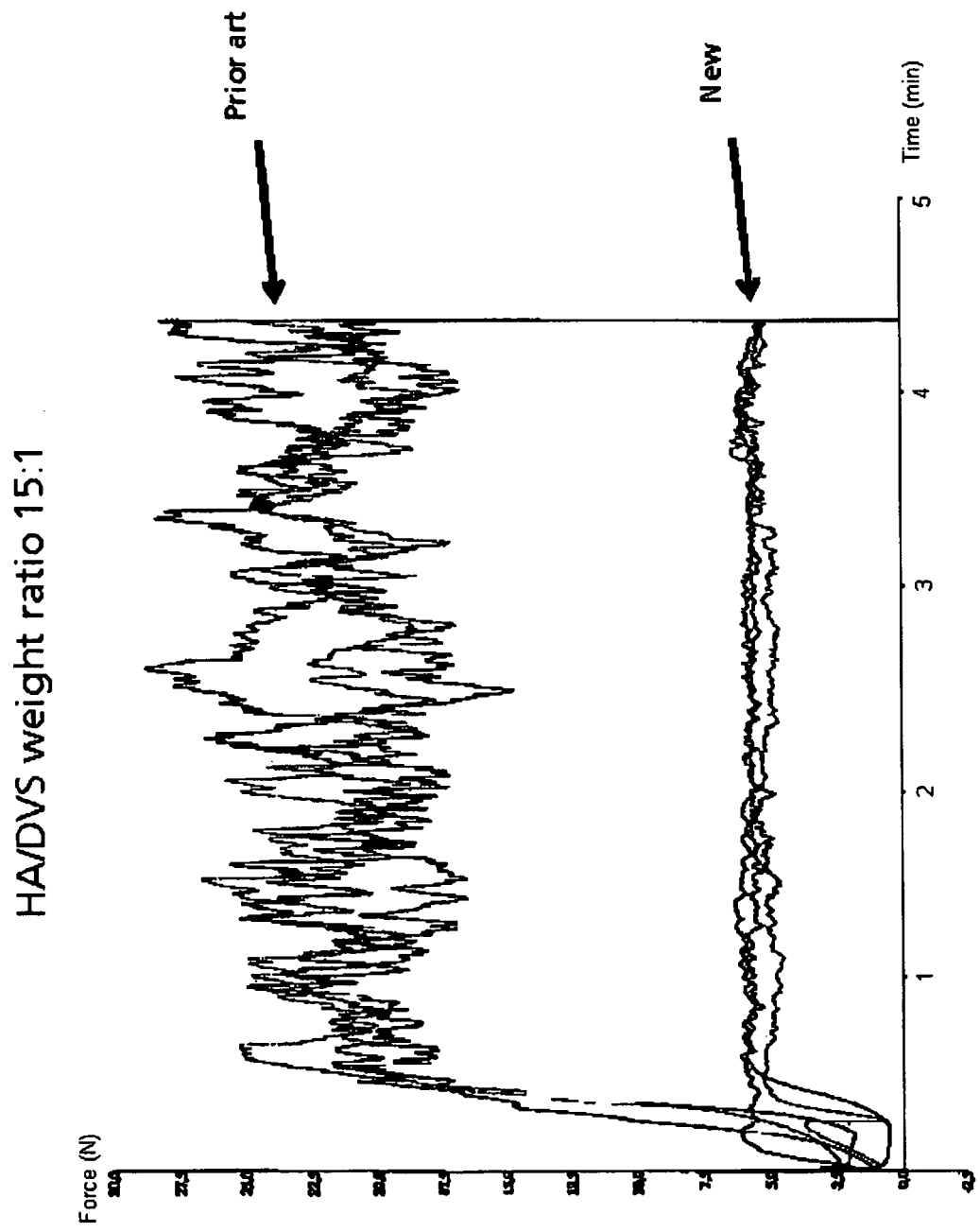

FIG. 5 shows the syringeability of DVS cross-linked HA hydrogels (HA/DVS 15:1, wt) prepared following the process described in example 2 herein ('new, heated'), and a hydrogel prepared according to the prior art (see U.S. Pat. No. 4,582,865, example 1) without heating, as described in example 9 below. The y-axis shows the injection force in Newton, beginning at 0.0 with increments of 2.5, and ending at 30.0.

DETAILED DESCRIPTION OF THE INVENTION

The first aspect of the invention relates to a method of producing a hydrogel comprising hyaluronic acid, or salt thereof, crosslinked with divinylsulfone (DVS), said method comprising the steps of:
(a) providing an alkaline solution of hyaluronic acid, or salt thereof;
(b) adding DVS to the solution of step (a), whereby the hyaluronic acid, or salt thereof, is crosslinked with the DVS to form a gel;
(c) treating the gel of step (b) with a buffer, wherein the gel swells and forms a hydrogel comprising hyaluronic acid, or salt thereof, crosslinked with DVS.

It has previously been described how to produce hyaluronic acid recombinantly in a *Bacillus* host cell, see WO 2003/054163, Novozymes A/S, which is incorporated herein in its entirety.

Accordingly, in a preferred embodiment, the invention relates to the method of the first aspect, wherein the hyaluronic acid, or salt thereof, is recombinantly produced in a *Bacillus* host cell.

Various molecular weight fractions of hyaluronic acid have been described as advantageous for specific purposes.

A preferred embodiment of the invention relates to a method of the first aspect, wherein the hyaluronic acid, or salt thereof, has an average molecular weight of between 100 and 3,000 kDa, preferably between 500 and 2,000 kDa, and most preferably between 700 and 1,800 kDa.

The initial concentration of hyaluronic acid, or a salt thereof, in the method of the invention, influences the properties of the resulting crosslinked gel, and of the swollen hydrogel.

Therefore, a preferred embodiment of the invention relates to a method of the first aspect, wherein the alkaline solution comprises dissolved hyaluronic acid, or salt thereof, in a concentration of between 0.1%-40% (w/v).

The pH value during the crosslinking reaction also influences the outcome, so in a preferred embodiment the invention relates to a method of the first aspect, wherein the alkaline solution comprises dissolved sodium hydroxide in a concentration of between 0.001-2.0 M.

It is also noteworthy that the concentration of the crosslinking agent has a profound impact on the resulting gels.

Consequently, a preferred embodiment of the invention relates to a method of the first aspect, wherein DVS is added to the solution of step (a) in a weight ratio of between 1:1 and 100:1 of HA/DVS (dry weight), preferably between 2:1 and 50:1 of HA/DVS (dry weight).

The inventors found that an initial period of stirring during and/or immediately after adding the DVS to the HA-solution was desirable to achieve satisfactory gelling.

Accordingly, a preferred embodiment of the invention relates to a method of the first aspect, wherein DVS is added with stirring to the solution of step (a), and wherein the solution temperature is maintained in the range of 5° C.-50° C., preferably in the range of 15° C.-40° C., more preferably in the range of 20° C.-30° C.; preferably the stirring is continued for a period of between 1-180 minutes.

In another preferred embodiment of the method of the first aspect, the DVS is added without stirring to the solution of step (a).

The present inventors determined that a heating step was beneficial after addition of the DVS to the solution.

Accordingly, a preferred embodiment of the invention relates to a method of the first aspect, wherein the solution temperature in step (b) is heated to a temperature in the range of 20° C.-100° C., preferably in the range of 25° C.-80° C., more preferably in the range of 30° C.-60° C., and most preferably in the range of 35° C.-55° C., and wherein the temperature is maintained in this range for a period of at least 5 minutes, preferably at least 10 minutes, 20 minutes, 30, 40, 50, 60, 70, 80, 90, 100, 110, 120, 130, 140, 150, 160, 170, or most preferably at least 180 minutes; preferably without stirring.

It is advantageous to leave the gel standing at room temperature for a brief period after the crosslinking reaction has taken place.

In a preferred embodiment of the method of the first aspect, the gel is maintained for a period of at least 5 minutes, preferably at least 10 minutes, 20 minutes, 30, 40, 50, 60, 70, 80, 90, 100, 110, 120, 130, 140, 150, 160, 170, or most preferably at least 180 minutes, at a temperature in the range of 0° C.-40° C., preferably in the range of 10° C.-30° C.

Many types of buffers, as are well known to the skilled person, have been envisioned as suitable for the swelling and neutralizing of the crosslinked gel of the invention. In a preferred embodiment the buffer comprises a buffer with a pH value in the range of 2.0-8.0, preferably in the range of 5.0-7.5.

Optimally, a suitable buffer is chosen with a pH value, which results in that the swollen hydrogel has a pH value as close to neutral as possible. In a preferred embodiment, the buffer comprises a buffer with a pH value, which results in that the hydrogel has a pH value between 5.0 and 7.5.

It is preferred that the buffer in the method of the first aspect comprises a phosphate buffer and/or a saline buffer.

In the swelling step the buffer must have a sufficient volume for it to accommodate the swelling gel until the gel is fully swollen. Accordingly, in a preferred embodiment of the method of the first aspect, the buffer in step (c) has a volume of at least 3 times the volume of the gel of step (b).

In a preferred embodiment of the method of the first aspect, the swelling in step (c) is carried out at a temperature of between 20° C.-50° C. for a period of at least 5 minutes, preferably at least 10 minutes, 20 minutes, 30, 40, 50, 60, 70, 80, 90, 100, 110, 120, 130, 140, 150, 160, 170, or most preferably at least 180 minutes.

It is also a preferred that the hydrogel formed in step (c) is washed at least once with water, water and a phosphate buffer, water and a saline buffer, or water and a phosphate buffer and a saline buffer, with a pH value in the range of 2.0-8.0, preferably in the range of 5.0-7.5.

EXAMPLES

Example 1

Preparation of DVS-Crosslinked HA Hydrogels

This example illustrates the preparation of DVS-crosslinked HA hydrogels with concomitant swelling and pH adjustment.

Sodium hyaluronate (HA, 770 kDa, 1 g) was dissolved into 0.2M NaOH to give a 4% (w/v) solution, which was stirred at room temperature, i.e. about 20° C., for 1 h. Three replicates were prepared. Divinylsulfone (DVS) was then added to the HA solutions in sufficient amount to give HA/DVS weight ratios of 10:1, 7:1, and 5:1, respectively. The mixtures were stirred at room temperature for 5 min and then allowed to stand at room temperature for 1 h. The gels were then swollen in 160 mL phosphate buffer (pH 4.5 or 6.5) for 24 h, as indicated in Table 1.

TABLE 1

Conditions for DVS-HA hydrogel preparation.

| Gel ID | HA/DVS weight ratio | Phosphate buffer used for swelling |
|---|---|---|
| 1 | 5:1 | 160 ml (pH 4.5) |
| 2 | 7:1 | 80 ml (pH 4.5) + 80 ml (pH 6.5) |
| 3 | 10:1 | 160 ml (pH 6.5) |

The pH of the gels was stabilized during the swelling step. After swelling, any excess buffer was removed by filtration and the hydrogels were briefly homogenized with an IKA® ULTRA-TURRAX® T25 homogenizer (Ika Labortechnik, DE). The volume and pH of the gels were measured (see Table 2).

TABLE 2

Characteristics of DVS-HA hydrogels.

| Gel ID | HA/DVS weight ratio | Volume of swollen gel | HA concentration (w/v) | pH | Appearance | Softness |
|---|---|---|---|---|---|---|
| 1 | 5:1 | 70 mL | 1.4% | 7.1 | Transparent, homogenous | + |
| 2 | 7:1 | 70 mL | 1.4% | 7.6 | Transparent, homogenous | ++ |
| 3 | 10:1 | 70 mL | 1.4% | 7.5 | Transparent, homogenous | +++ |

The pH of the hydrogels ranged from 7.1 to 7.6 (table 2), which confirms that the swelling step can be utilized to adjust the pH in this process. All the hydrogels occupied a volume of 70 mL, which corresponds to a HA concentration of ca. 1.4% (w/v). They were transparent, coherent and homogenous. Softness increased with decreasing cross-linking degree (Table 2).

Example 2

Preparation of Homogenous DVS-Crosslinked HA Hydrogels

This example illustrates the preparation of highly homogenous DVS-cross-linked HA hydrogels.

Sodium hyaluronate (770 kDa, 2 g) was dissolved into 0.2M NaOH with stirring for approx. 1 hour at room temperature to give a 8% (w/v) solution. DVS was then added so that the HA/DVS weight ratio was 7:1. After stirring at room temperature for 5 min, one of the samples was heat treated at 50° C. for 2 h without stirring, and then allowed to stand at room temperature overnight. The resulting cross-linked gel was swollen into 200 ml phosphate buffer (pH 5.5) 37° C. for 42 or 55 h, and finally washed twice with 100 ml water, which was discarded. Volume and pH were measured, as well as the pressure force necessary to push the gels through a 27G*½ injection needle (see Table 3).

TABLE 3

Characteristics of DVS-cross-linked HA hydrogels.

| Gel ID | Heat treated | Volume of swollen gel | HA concentration (w/v) | pH | Appearance | Softness | Stability of pressure force during injection |
|---|---|---|---|---|---|---|---|
| 1 | Yes | 145 mL | 1.4% | 6.1 | Transparent, homogenous | +++ | +++ |
| 2 | No | 90 mL | 1.1% | 6.7 | Transparent, homogenous | + | + |

The cross-linked HA hydrogel prepared according to this example exhibited a higher swelling ratio and an increased softness compared to a control hydrogel which was not heat treated (Table 3). The pressure force applied during injection through a 27G*½ needle was more stable than that of the latter sample, indicating that the cross-linked HA hydrogel is more homogenous.

Example 3

Biostability of DVS-Crosslinked HA Hydrogels

This example illustrates the in vitro biostability of DVS-cross-linked HA hydrogels using enzymatic degradation.

A bovine testes hyaluronidase (HAase) solution (100 U/mL) was prepared in 30 mM citric acid, 150 mM $Na_2HPO_4$, and 150 mM NaCl (pH 6.3). DVS-HA cross-linked hydrogel samples (ca. 1 mL) were placed into safe-lock glass vials, freeze-dried, and weighed ($W_0$; Formula 1). The enzyme solution (4 mL, 400 U) was then added to each sample and the vials were incubated at 37° C. under gentle shaking (100-200 rpm). At predetermined time intervals, the supernatant was removed and the samples were washed thoroughly with distilled water to remove residual salts, they were then freeze-dried, and finally weighed ($W_t$; Formula 1).

The biodegradation is expressed as the ratio of weight loss to the initial weight of the sample (Formula 1). Weight loss was calculated from the decrease of weight of each sample before and after the enzymatic degradation test. Each biodegradation experiment was repeated three times.

$$\text{Weightloss (\%)} = \frac{W0 - Wt}{W0} \times 100 \qquad \text{Formula 1}$$

Figure 1:
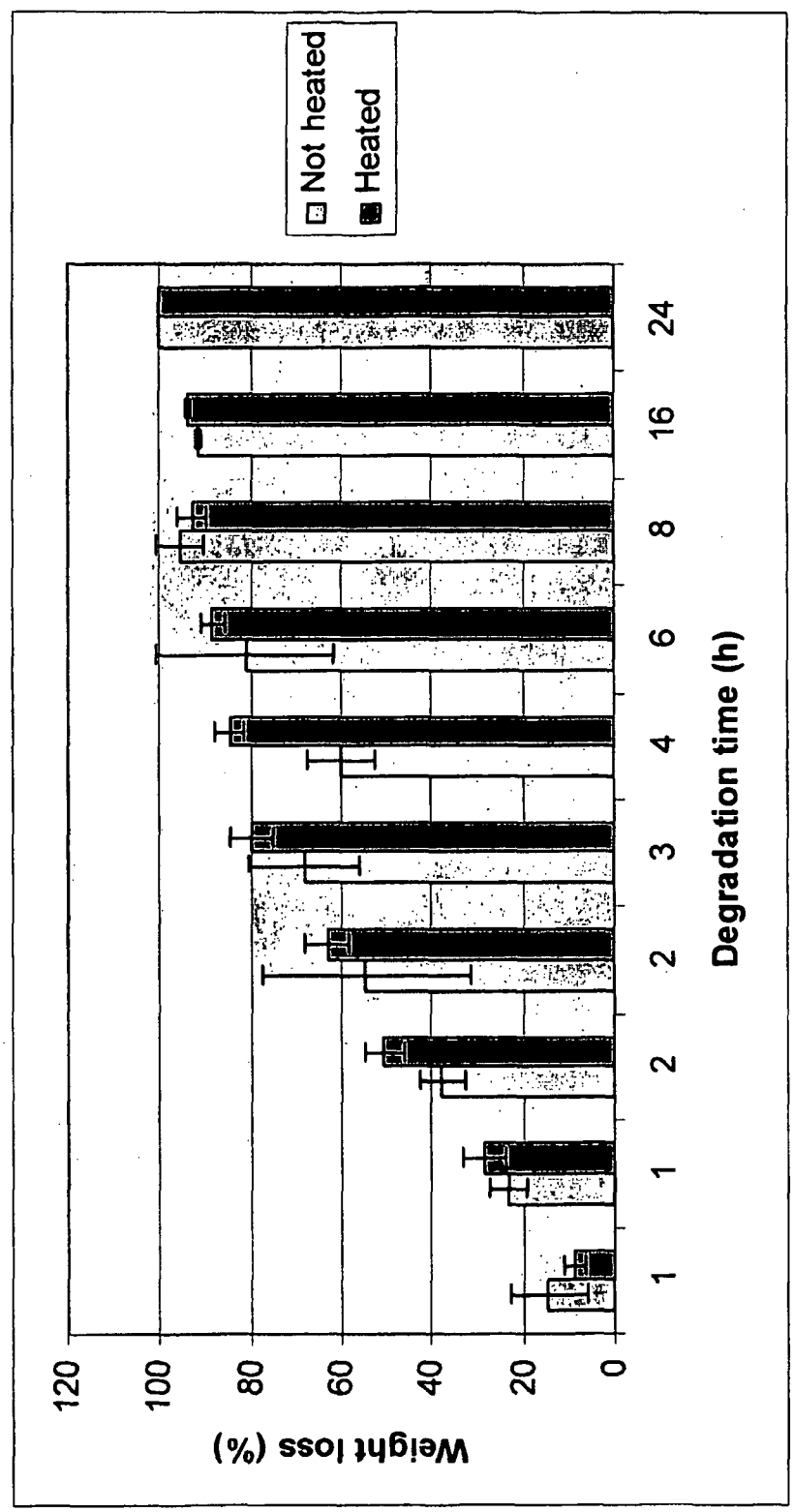
FIG. 1 illustrates the weight loss of DVS-HA hydrogels resulting from Hyaluronidase degradation as a function of time. DVS-HA hydrogels prepared with a heating step ('Heated'), as described in Example 2, were compared to DVS-HA hydrogels which had not been heat treated ('Not heated').

The results are shown in table 4, as well as in FIG. 1, which illustrates the weight loss of DVS-HA hydrogels resulting from HAase degradation as a function of time. DVS-HA hydrogels prepared as described in example 2 ('Heated') were compared to DVS-HA hydrogels which had not been heat treated ('Not heated'). For both types of gel, degradation was fast during the first four hours, and then proceeded slower until completion at 24 h. Importantly there was a significant variation of the weight loss values for the samples which had not been heated as compared to the hydrogel prepared with a heating step as described in example 2. This clearly illustrates that a highly homogenous DVS-cross-linked HA hydrogel is obtained by using the process described in example 2.

Example 4

Preparation of Water-in-Oil Emulsions for Cosmetics

In this and in the following example, DVS-crosslinked HA hydrogels were formulated into creams and serums, that when applied to the skin increase the skin moisturization and elasticity, and provide immediate anti-aging effect, as well as film-forming effect.

A typical formulation of a water-in-oil (w/o) emulsion containing 2% DVS-cross-linked HA. Each phase (A to E) was prepared separately by mixing the defined ingredients (see Table 4). Phase B was then added to phase A under stirring with a mechanical propel stirring device and at a temperature less than 40° C. Phase C was then added followed by phase D and finally phase E under stirring. Formulations were also made, wherein the HA hydrogel concentration was 4%, 6% and 8%, respectively, in Phase D, to give a range of w/o formulations.

TABLE 4

| Phase | Ingredient | Proportion (w/w) | Function |
|---|---|---|---|
| A | Cyclopentasiloxane, dimethicone | 10% | Emollient |
|   | Cyclopentasiloxane | 15% | Emollient |
|   | Cyclopentasiloxane and PEG/PPG-20/15 Dimethicone | 4% | Emulsifier |
|   | Hydrogenated polydecene | 8% | Emollient |
| B | Water | 49.3% | |
|   | Sodium chloride | 0.2% | |
| C | Tocopheryl acetate | 0.5% | Antioxidant |
| D | DVS Cross-linked sodium hyaluronate | 2% | |
|   | Water | 10% | |
| E | Phenoxyethanol, ethylhexylglycerin | 1% | Preservative |

Another typical formulation of a w/o-emulsion containing 2% DVS-crosslinked HA is shown in table 5. Each phase (A to F) in table 5 was prepared separately by mixing the defined ingredients (see Table 5). Phase B was mixed with phase A and the resulting oil phase was heated at 75° C. Phase C was also heated to 75° C. The oil phase was added to phase C at 75° C. under stirring with a mechanical propel stirring device. The emulsion was then cooled down to less than 40° C., after which phase D was added, followed by phase E and finally phase F under stirring. Formulations were also made, wherein the HA hydrogel concentration was 4%, 6% and 8%, respectively, in Phase E, to give a range of w/o formulations.

TABLE 5

| Phase | Ingredient | Proportion (w/w) | Function |
|---|---|---|---|
| A | Hydrogenated polydecene | 18% | Emollient |
|   | Acrylates/C10-30 alkyl acrylate crosspolymer | 1% | Thickener |
| B | Sodium cocoyl Glutamate | 10% | Emulsifier |
| C | Aqua | 53.5% | |
|   | Distarch Phosphate | 2% | Texture agent |
| D | Tocopheryl acetate | 0.5% | Antioxidant |
|   | Cyclopentasiloxane, dimethicone | 2% | Feeling and spreading agent |
| E | Cross-linked sodium hyaluronate | 2% | |
|   | Aqua | 10% | |
| F | Phenoxyethanol, ethylhexylglycerin | 1% | Preservative |

Example 5

Preparation of Silicone Serums

A typical formulation of a silicone serum containing 2% DVS-cross-linked HA was prepared as shown in table 6. All ingredients were mixed at the same time under very high stirring and at less than 40° C. (see table 6). Formulations were also prepared, wherein the HA hydrogel concentration was 4%, 6% and 8%, respectively, to give a range of serums.

TABLE 6

| Ingredient | Proportion (w/w) | Function |
|---|---|---|
| Cyclopentasiloxane C30-45 Alkyl Cetearyl Dimethicone Crosspolymer | 60% | Line blurring effect, thickener, vehicle |
| Cyclopentasiloxane | 34.5% | Vehicle, emollient |
| Polymethylsilsesquioxane | 2.5% | Soft powdery feel |
| Cross-linked sodium hyaluronate | 2% | |
| Phenoxyethanol, ethylhexylglycerin | 1% | Preservative |

Example 6 pH Equilibration During Swelling; a Kinetics Study

A kinetics study showed that DVS cross-linked HA hydrogels with neutral pH are obtained after swelling in phosphate buffer (pH 7.0) for 8 to 14 hours, depending on the degree of cross-linking. A set of DVS cross-linked hydrogels was prepared as described in the above, using from 4 to 8% HA solution, and using various amounts of DVS cross-linker, as indicated in Table 7.

TABLE 7

| Entry | Initial HA concentration (w/v) | HA/DVS weight ratio |
|---|---|---|
| 1 | 4% | 2.5:1 |
| 2 | 6% | 15:1 |
| 3 | 8% | 15:1 |
| 4 | 6% | 10:1 |

Figure 2:
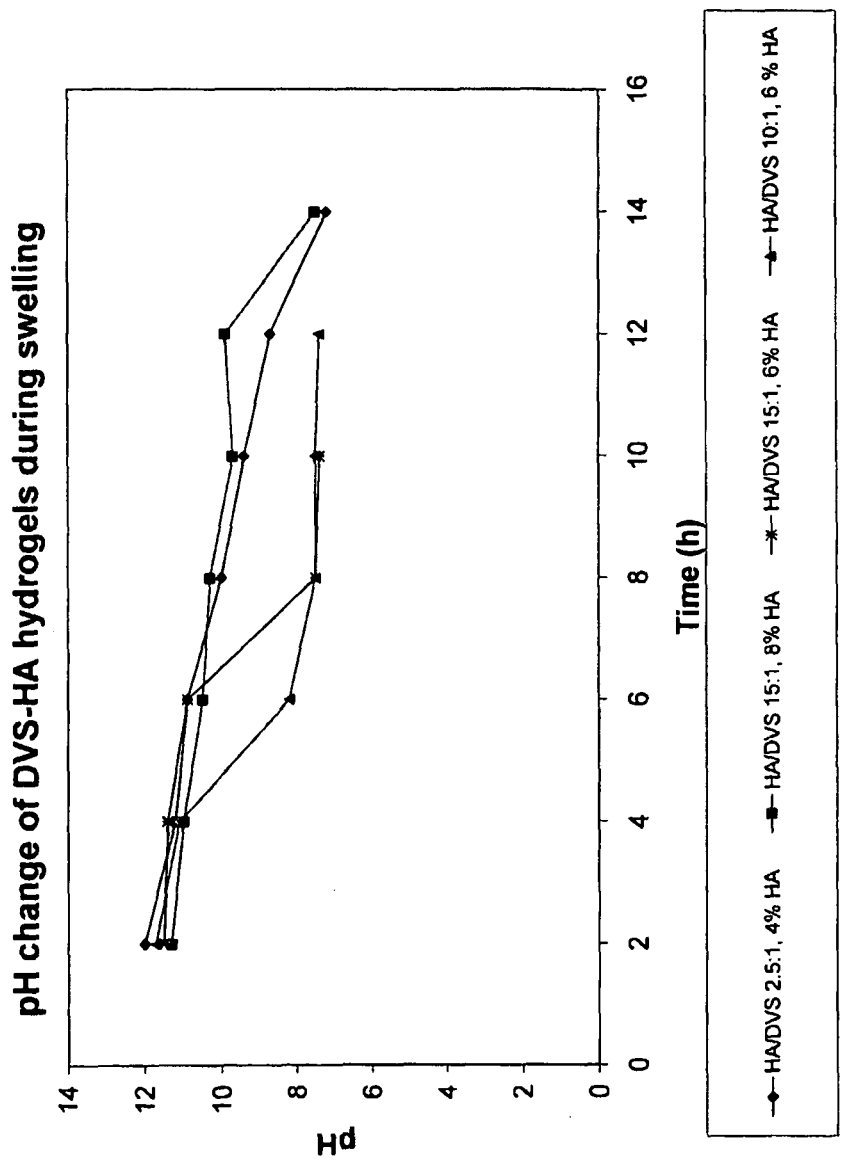
FIG. 2 shows the time course of the pH-value of a set of DVS crosslinked HA hydrogels with different ratios or degrees of crosslinking, during swelling in phosphate buffer (pH=7.0), as described in detail in Example 6 below.

At regular intervals (every 2 hours), the hydrogels were removed during the heat-treatment and decanted, and pH was measured (see FIG. 2). Fresh swelling buffer was used after each measurement. The results show that, for all hydrogels, pH ranged between 11 and 12 after 2-hours of swelling. Then pH gradually decreased to 7.2-7.5.

The decrease was faster for the hydrogels that were less cross-linked, i.e., where the HA/DVS-ratio was higher. The decrease in pH is shown for the HA 6% solution and two different ratios of HA/DVS in FIG. 2, where the HA/DVS ratio of 10:1 is labelled with triangles, and 15:1 is labelled with squares. In these two cases, pH was neutralized within 8 hours. In contrast, neutral pH was reached after 14 hour-swelling for hydrogels with either a higher HA concentration (e.g. 8%) or a higher degree of cross-linking (e.g. HA/DVS ratio of 2.5). These observations are in accordance with the fact that HA molecules in the low cross-linked hydrogels exhibit greater freedom and flexibility, allowing good hydration and thereby faster pH equilibration.

Example 7

Visco Elastic Properties of Hydrogels Based on DVS-Crosslinked HA

The rheological measurements were performed on a Physica MCR 301 rheometer (Anton Paar, Ostfildern, Germany) using a plate-plate geometry and at a controlled temperature of 25° C. The visco-elastic behavior of the samples was investigated by dynamic amplitude shear oscillatory tests, in which the material was subjected to a sinusoidal shear strain. First, strain/amplitude sweep experiments were performed to evaluate the region of deformation in which the linear viscoelasticity is valid. The strain typically ranged from 0.01 to 200% and the frequency was set to 1 Hz. Then, in the linear visco-elastic regions, the shear storage modulus (or elastic modulus G') and the shear loss modulus (or viscous modulus, G") values were recorded from frequency sweep experiments at a constant shear strain (10%) and at a frequency between 0.1 and 10 Hz. The geometry, the NF and the gap were PP 25, 2 and 1 mm, respectively.

G' gives information about the elasticity or the energy stored in the material during deformation, whereas G" describes the viscous character or the energy dissipated as heat. In particular, the elastic modulus gives information about the capability of the sample to sustain load and return in the initial configuration after an imposed stress or deformation. In all experiments, each sample was measured at least three times.

The results (FIG. 3) showed that for both hydrogels:
G'>G" and
G' is ALMOST independent of the frequency.

In case of the hydrogel with a higher degree of cross-linking (i.e. lower HA/DVS ratio: 10/1) G' is one order of magnitude higher than G", indicating that this sample behaves as a strong gel material. Briefly, the overall rheological response is due to the contributions of physical and chemical crosslinks, and to topological interactions among the HA macromolecules. The interactions among the chains bring about a reduction of their intrinsic mobility that is not able to release stress, and consequently the material behaves as a three-dimensional network, where the principal mode of accommodation of the applied stress is by network deformation. Moreover, this hydrogel was more elastic than that with a lower degree of cross-linking (i.e., higher ratio of HA/DVS: 15:1). Indeed, the higher the number of permanent covalent cross-links, the larger the number of entanglements, and therefore the higher the elastic response of the hydrogel.

Example 8

Network Structural Parameters

In this experiment, the viscoelastic properties were evaluated on a rotational rheometer (Gemini, Bohlin Instruments, UK) using a parallel plate geometry (PP30 cell). The tests were carried out at the controlled temperature of 25° C. using a thermostatic bath. To avoid water evaporation, the humidity of the chamber containing the samples was controlled by a humidity Control Accessory.

The hydrogels were subjected to periodic oscillation in a dynamic experiment (small amplitude frequency sweep tests) to evaluate the dependence of the elastic and viscous moduli, G' and G". The frequency range was 0.01 Hz-10 Hz. In order to identify the linear viscoelastic response range of the materials, preliminary strain sweep tests were performed on the samples at the oscillation frequency of 1 Hz. The tests were repeated at least three times on each sample.

The values of the elastic modulus can be used to estimate the parameter of the network structure. As G is proportional to the number of entanglements (Ferry, 1980), the elastic modulus can be expressed through:

$$G \cong R \cdot T \cdot z \qquad \text{Formula 2}$$

Wherein RT is the thermal energy, and z is the number of the entanglement points or cross-linking point expressed in mol/volume. The parameter z can be calculated by:

$$z \approx \frac{c}{M_e} \qquad \text{Formula 3}$$

Wherein c is the polymer concentration, and $M_e$ is the average molecular weight of the polymer segments between two entanglements. Substituting in Formula 2, $M_e$ can be estimated by the following equation:

$$M_e \cong \frac{R \cdot T \cdot c}{G} \qquad \text{Formula 4}$$

To calculate G by means of Formula 4, the validity of the rubber elasticity theory was assumed and the temporary network of gel-like material was presumed to behave as does vulcanized rubber upon stimulus of a time scale shorter than the life time of the entanglement network (Flory, 1953). The "dangling ends", which are the polymer chain segments attached to the network by only one entanglement point, do not contribute to the G value because they cannot store elastic energy. Thus, a correction is needed in Formula 4 (Flory, 1953):

$$G \cong \frac{R \cdot T \cdot c}{M_d}\left(1 - 2\frac{M_d}{M_n}\right) \qquad \text{Formula 5}$$

Where Mn is the number average molecular weight. Using the "equivalent network model" (Schurz, 1991), it is possible to estimate DN which is the average distance between the entanglements points in a idealized "equivalent network":

$$D_N = \sqrt[3]{\frac{6 \cdot M_d}{\pi \cdot c \cdot A}} \qquad \text{Formula 6}$$

Wherein A is Avogadro's number.

The results of $D_N$ and $M_d$ are reported in table 8. It can be noticed that the higher $M_d$ (248120 g/mol) and higher Dn (46 nm) are obtained for sample 1. Sample 2 had the lowest Md (204000) and a Dn value of 43.5 nm. Samples 3 and 4, which have the same elastic modulus, are characterized by Md of 240000 g/mol and Dn of 42 nm.

TABLE 8

Network parameters for DVS-HA hydrogels.

| Sample ID | Initial HA conc. (w/v) | HA/DVS wt ratio | Phosphate buffer concentration[a] | G' [Pa][b] | HA concentration (g/l) | Md (g/mol) | $D_N$ (nm) |
|---|---|---|---|---|---|---|---|
| 1 | 4% | 2.5:1 | 50 mM | 11 | 8 | 248120 | 46 |
| 2 | 6% | 10:1 | 50 mM | 27.7 | 7.8 | 204000 | 43.5 |
| 3 | 4% | 2.5:1 | 150 mM | 18 | 10 | 238000 | 42 |
| 4 | 6% | 10:1 | 150 mM | 18 | 10.7 | 240700 | 41.5 |

[a]During swelling;
[b]Value of the elastic modulus at 0.1 Hz.

Example 9

Syringeability of DVS-Crosslinked HA Hydrogels

The syringeability of DVS cross-linked HA hydrogels prepared according to the present invention was compared to that of hydrogels prepared according to prior art, e.g., as in example 1 of U.S. Pat. No. 4,582,865.

The syringeability was measured on a Texture analyzer (Stable Micro Systems, TA. XT Plus) as the force (in N) needed to inject the hydrogel through a 27G½ needle over a distance of 55 mm at a speed of 12.5 mm/min. Hydrogel samples were transferred into a 1 mL-syringe fitted with a 27G½ needle and the syringe was placed in the holder. Each sample was measured three times. FIGS. 4 and 5 illustrate the syringeability of DVS cross-linked HA hydrogels with HA/DVS weight ratios of 10:1 and 15:1, respectively.

The injection profiles recorded in FIGS. 4 and 5 are characteristic of the sample homogeneity. Indeed, the more stable the applied injection force is, the more homogenous the hydrogel is. Moreover, a low force corresponds to an easy injection of the hydrogel by the operator.

The results clearly indicated that the DVS HA-hydrogels produced according to the process described herein were far more homogenous than those obtained from prior art method. Note, that the prior art samples had to be homogenized mechanically in order for them to be syringeable at all. This homogenization created small particles, the presence of which lead to very irregular injection profiles.

Furthermore, the cross-linked hydrogels prepared according to the present invention were easier to inject through a fine needle, as demonstrated by the lower force required. It is noteworthy that the injection force increases with an increasing degree of cross-linking due to the formation of a stronger network.

Example 10

Formulations of Crosslinked DVS-HA Hydrogels for Local Ophthalmology

A typical formulation of a 500 mL eye-drop solution containing 1% (w/v) DVS-cross-linked HA is shown in table 9. All ingredients were weighed and transferred into a 500 mL volumetric flask. Water (300 mL) was added and the mixture was stirred at room temperature for 5 h. pH was adjusted to 7.2 with 2M NaOH and the volume was adjusted to exactly 500 mL with milliQ water.

TABLE 9

| Ingredient | Amount | Function |
|---|---|---|
| Cross-linked sodium hyaluronate | 5 g | Lubricant Viscosity enhancer Moisturizer/hydration agent |
| Sodium ethylene diamine tetra acetate (EDTA) | 50 mg | Chelating agent |
| Sodium dihydrogen phosphate dihydrate (NaH$_2$PO$_4$, 2H$_2$O) | 20 mg | Buffer |
| Disodium hydrogen phosphate dihydrate (Na$_2$HPO$_4$, 2H$_2$O) | 140 mg | Buffer |
| Sodium chloride | 4.5 g | |
| Polyaminopropyl Biguanide (PHMB) | 3.25 microL | Preservative |
| Milli-Q water | Up to 500 mL | |

Example 11

Crosslinked HA/DVS Hydrogel with Preservative

A DVS-cross-linked HA hydrogel was prepared using 1.5 g of sodium HA in 0.2 M NaOH to give a 6% (w/v) solution. The HA/DVS weight ratio was 10:1. The hydrogel was prepared in three replicates according to the procedure described in example 2 until the swelling step, after which it was treated as follows: After incubation in an oven at 50° C. for two hours, the hydrogel was immersed into Na2HPO4/NaH2PO4 buffer (1 L, 50 mM, pH 7.0) containing the preservative (2-phenoxy-ethanol/3[(2-ethylhexyl)oxy]1,2-propanediol).

The concentration of preservative was 10 mL/mL to target a final concentration of 1% (v/v) in the swollen hydrogel. It was anticipated that the preservative would diffuse into the hydrogel during the incubation, and that at the same time, microbial contamination in the buffer would be prevented.

The vessel was covered with parafilm and placed in an oven at 37° C. After 1 h, the swelling bath was removed and the hydrogel was swollen in a fresh phosphate buffer containing 10 mL/mL preservative for 6-7 h. This step was repeated until the swelling time was 12 h, whereafter the pH was measured. Swelling was continued for another 2.5 h to reach neutral pH.

The amount of preservative incorporated into the hydrogel was determined by UV-spectrophotometry (Thermo Electron, Nicolet, Evolution 900, equipment nr. 246-90). A 1% (v/v) solution of the preservative in phosphate buffer was first analyzed to select the wavelength. Approximately 5 mL of hydrogel were collected using a pipette. Typically, samples were collected in the center of the swollen round hydrogel, and in the north, east, south, and west "sides" of the round gel.

The samples were then transferred into a cuvette and the absorbance was read at 292 nm. Each sample was read three times and the absorbance was zeroed against a blank DVS-cross-linked HA hydrogel, containing no preservative.

The results showed that the amount of preservative incorporated in the DVS-HA hydrogel ranged between 0.91% and 1.02% (see Table 10). There was very good reproducibility between the replicates. Importantly, no significant difference between samples from the same hydrogel was observed, indicating a homogenous diffusion of the preservative into the hydrogel.

TABLE 10

Amount of incorporated preservative into DVS-HA hydrogel upon swelling in a 1% preservative-spiked phosphate buffer for 14.5 h.

| Sample ID | Sample site | Absorbance* (292 nm) | Preservative concentration (%, v/v) | Average concentration (%, v/v) |
|---|---|---|---|---|
| Replicate 1 | Center | 0.072 | 1.02 | 0.91 |
| | Side | 0.058 | 0.82 | |
| | Side | 0.066 | 0.94 | |
| | Side | 0.057 | 0.81 | |
| | Side | 0.068 | 0.97 | |
| Replicate 2 | Middle | 0.076 | 1.08 | 1.02 |
| | Side | 0.069 | 0.98 | |
| | Side | 0.082 | 1.17 | |
| | Side | 0.071 | 1.01 | |
| | Side | 0.062 | 0.88 | |
| Replicate 3 | Middle | 0.083 | 1.18 | 1.02 |
| | Side | 0.074 | 1.05 | |
| | Side | 0.069 | 0.98 | |
| | Side | 0.066 | 0.94 | |
| | Side | 0.068 | 0.97 | |

*The absorbance is the mean value of three measurements performed on the same sample.

The invention claimed is:

1. A method of producing a hydrogel comprising hyaluronic acid or a salt thereof, cross-linked with divinylsulfone (DVS), said method comprising the steps of:
   (a) providing an alkaline solution of hyaluronic acid or salt thereof, wherein the alkaline solution comprises dissolved hyaluronic acid or salt thereof in a concentration of between 0.1-40% (w/v);
   (b) forming a gel of hyaluronic acid or salt thereof cross-linked with DVS by:
      (i) adding DVS to the solution of step (a) in a weight ratio of between 1:1 and 100:1 of hyaluronic acid or salt thereof/DVS (dry weight) and stirring the solution of hyaluronic acid or salt thereof/DVS while the temperature of the solution of hyaluronic acid or salt thereof/DVS is maintained in the range of 15-30° C., wherein the stirring is for a period of 1-180 minutes; and (ii) heating the hyaluronic acid or salt thereof/DVS solution of step (i) to a temperature in the range of 35-55° C., and maintaining the temperature in the range of 35-55° C. for at least 5 minutes; and (c) forming a hydrogel comprising the hyaluronic acid or salt thereof, cross-linked with DVS by treating the gel of produced from step (b) with a buffer to swell the gel and form a hydrogel.

2. The method of claim 1, wherein the hyaluronic acid or salt thereof is recombinantly produced in a *Bacillus* host cell.

3. The method of claim 1, wherein the hyaluronic acid or salt thereof has an average molecular weight of between 100 and 3,000 kDa.

4. The method of claim 1, wherein the buffer comprises a buffer with a pH in the range of 2.0-8.0.

5. The method of claim 1, wherein the buffer comprises a buffer with a pH, which results in that the hydrogel has a pH between 5.0 and 7.5.

6. The method of claim 1, wherein the buffer comprises a phosphate buffer and/or a saline buffer.

7. The method of claim 1, wherein the alkaline solution comprises dissolved sodium hydroxide in a concentration of between 0.001-2.0 M.

8. The method of claim 1, wherein the buffer in step (c) has a volume of at least 3 times the volume of the gel of step (b).

9. The method of claim 1, wherein step (c) is carried out at a temperature of between 20-50° C., for a period of at least 5 minutes.

10. The method of claim 1, further comprising washing the hydrogel formed in step (c) at least once with water, and/or a phosphate and/or saline buffer with a pH in the range of 2.0-8.0.

11. The method of claim 1, wherein the stirring of step (b) is initiated during the addition of DVS.

12. The method of claim 1, wherein the stirring of step (b) is initiated immediately after the addition of DVS.

13. The method of claim 1, wherein there is no stirring during the heating of step (c).

14. The method of claim 1, wherein the temperature in the range of 35-55° C. is maintained for at least 10 minutes.

15. The method of claim 1, wherein temperature in the range of 35-55° C. is maintained for at least 20 minutes.

16. The method of claim 1, wherein temperature in the range of 35-55° C. is maintained for at least 30 minutes.

17. The method of claim 1, wherein the temperature in the range of 35-55° C. is maintained for at least 40 minutes.

18. The method of claim 1, wherein the temperature in the range of 35-55° C. is maintained for at least 50 minutes.

19. The method of claim 1, wherein the temperature in the range of 35-55° C. is maintained for at least 60 minutes.

20. The method of claim 1, wherein the temperature in the range of 35-55° C. is maintained for at least 120 minutes.

21. The method of claim 1, wherein the temperature in the range of 35-55° C. is maintained for at least 180 minutes.

* * * * *